United States Patent [19]

Lusterio et al.

[11] Patent Number: 5,439,816
[45] Date of Patent: Aug. 8, 1995

[54] CARBOXYMETHYLCELLULASE ISOLATED FROM BACILLUS SP. PKM-5430 (FERM BP-4087)

[75] Inventors: Decorosa D. Lusterio; Franklin G. Suizo, both of Cagayan de Oro; Nellie M. Labunos; Marietta N. Valledor, both of Misamis Oriental; Shinta Ueda, Cagayan de Oro, all of Philippines

[73] Assignee: Kao Corporation, Tokyo, Japan

[21] Appl. No.: 244,370

[22] PCT Filed: Dec. 10, 1992

[86] PCT No.: PCT/JP92/01615

§ 371 Date: Jun. 2, 1994

§ 102(e) Date: Jun. 2, 1994

[87] PCT Pub. No.: WO93/12224

PCT Pub. Date: Jun. 24, 1994

[30] Foreign Application Priority Data

Dec. 10, 1991 [JP] Japan .................. 3-325978
Dec. 10, 1991 [JP] Japan .................. 3-325979

[51] Int. Cl.$^6$ .................. C12N 9/42; C12N 1/20; C12N 1/00
[52] U.S. Cl. .................. 435/209; 435/252.31; 435/832
[58] Field of Search .................. 435/209, 252.31, 832

[56] References Cited

U.S. PATENT DOCUMENTS 5,231,022  7/1993  Saito et al. .................. 435/209

FOREIGN PATENT DOCUMENTS 63-146786  6/1988  Japan .
4-27387    1/1992  Japan .

OTHER PUBLICATIONS

Selby et al., *Gel Filtration of Cellulases,* vol. 94, 1965, pp. 578–583.
Okoshi et al., Agric. Biol. Chem., 54(1), 83–89, 1990.
Shikata et al., Agric. Biol. Chem., 54(1), 91–96, 1990.
Lusterio et al., BioSci, Biotech. Biochem., 56(10), 1671–1672, 1992.

*Primary Examiner*—David M. Naff
*Assistant Examiner*—Mike Meller
*Attorney, Agent, or Firm*—Oblon, Spivak, McClelland, Maier & Neustadt

[57] ABSTRACT

Carboxymethylcellulases 5430 and 5812 which show strong activity toward carboxymethylcellulose and lichenan, and moreover are broad in active pH range and active temperature range, stable in the presence of various surfactants and excellent in thermal stability and particularly, in alkali resistance. These enzymes can be advantageously used as formulation components for detergent compositions. The carboxymethylcellulases are isolated from Bacillus strains FERM BP-4087 and FERM BP-4088. Some of the characteristics of the enzymes include: a molecular weight of 26,000±1,000 as estimated by gel filtration on Bio-Gel A 0.5 m, the ability to hydrolyze carboxymethylcellulose, two optimum pH values of about 7.7 and 9.5, and a temperature optimum at about 55° C.

1 Claim, 8 Drawing Sheets

Figure 1

MacIlvaine buffer (pH: 3-7, ●)

0.1 M Tris-hydrochloride buffer (pH: 7-9, ○)

50 mM Sodium phosphate buffer (pH: 6-8, ▲)

0.1 M Glycine-sodium hydroxide buffer (pH: 8-11, △)

0.1 M Potassium chloride-sodium hydroxide buffer (pH: 9-14, ■)

MacIlvaine buffer (pH: 3-7, ●)

0.1 M Tris-hydrochloride buffer (pH: 7-9, ○)

50 mM Sodium phosphate buffer (pH: 6-8, ▲)

0.1 M Glycine-sodium hydroxide buffer (pH: 8-11, △)

0.1 M Potassium chloride-sodium hydroxide buffer (pH: 9-14, ■)

Addition of 10 mM CaCl$_2$, - ● -

No addition of CaCl$_2$, - ▲ -

CARBOXYMETHYLCELLULASE ISOLATED FROM BACILLUS SP. PKM-5430 (FERM BP-4087)

TECHNICAL FIELD

The present invention relates to new carboxymethylcellulases, and more specifically to new enzymes, carboxymethylcellulases, which are broad in active pH range and active temperature range and particularly, far excellent in pH stability and thermal stability, and microorganisms producing such enzymes.

BACKGROUND ART

Cellulases consist of a complex enzyme system which catalyzes an enzymatic reaction, in which celluloses and analogous polysaccharides thereof are hydrolyzed to glucose, or cellobiose or cello-oligosaccharides, and are understood to be a general term for enzymes referred to as $C_1$ enzymes, $C_x$ enzymes, $\beta$-glucosidases, exo-$\beta$-glucanases, endo-$\beta$-glucanases, cellobiases or the like according to their action mechanisms. Viewed from a historic light, the research of the cellulases has been devotedly advanced for a long time with a view toward putting biomass resources to good use. Fungi, for example, the genera Trichoderma, Aspergillus, Acremonium and Humicola have been required for sources of their supply. However, cellulases from microorganisms including fungi have specificity on action of their constitutive enzyme groups and diversity on their physicochemical properties and the like. Therefore, their actual conditions can be yet hardly said to have been made clear.

Among the cellulases, those particularly high in action on carboxymethylcellulose, i.e., endo-type hydrolytic action, are called carboxymethylcellulases. In recent years, an application to, for example, an additive for laundry detergents has been developed as a new industrial use for the cellulases including carboxymethyl-cellulases. Judging from the above-described cellulases from microorganisms, however, most of cellulases produced from microorganisms in natural world show optimum activities at acidic pHs and are deactivated at alkaline pHs. Namely, they are acidic cellulases (optimum active pH: 4–6). Under the circumstances, there has been found only few alkaline cellulases and alkali-resistant cellulases, suitable for use in laundry detergent which gives alkaline pHs.

The term "alkaline cellulase" used herein is intended to mean one whose optimum pH is in an alkaline range, and the term "alkali-resistant cellulase" means one whose optimum pH is in a neutral to acidic range, but which has a satisfactory activity in an alkaline region as compared with an activity at an optimum pH and is maintained stable.

Namely, there have heretofore been reported only, as processes for the production of alkaline cellulases and alkali-resistant cellulases, which can be used in laundry detergent compositions, a process in which an alkaliphilic species of the genus Bacillus is incubated to collect Cellulase A (Japanese Patent Application Laid-Open No. 28515/1975), a process in which an alkaliphilic species belonging to the genus Cellulomonas is incubated to produce alkaline Cellulase 301-A (japanese Patent Application Laid-Open No. 224686/1983), a process in which alkaliphilic Bacillus No. 1139 is incubated to produce a carboxymethylcellulase [F. Fukumori, T. Kudo and K. Horikoshi, J. Gen. Microbiol., 131, 3339(1985)], and a process in which a species of the genus Streptomyces is used to produce an alkaline cellulase (Japanese Patent Application Laid-Open No. 19483/1986). None of these processes were suitable for use in industrial production by fermentation.

On the other hand, it has recently been reported that Bacillus sp. KSM-635 (FRI Deposition No. 8872), which is a species of alkaliphilic microorganisms, effectively produces a carboxymethylcellulase suitable for use in laundry detergent compositions and moreover, the carboxymethylcellulase can be provided with higher yield by suitably selecting incubation conditions, thereby permitting its commercial and industrial production by fermentation.

However, the carboxymethylcellulase from the above-described Bacillus sp. KSM-635 shows an optimum active temperature of about 40° C. and is suitable for low-temperature washing. On the other hand, there is a demand for an enzyme capable of using in laundry detergents at higher temperatures. In addition, it is desired that a carboxymethylcellulase having high stability at higher pH values should be found because the detergency of detergent generally becomes enhanced at higher pH values.

Therefore, it is an object of this invention to provide a carboxymethylcellulase capable of acting even at high temperatures, broad in active pH range and in particular, good in stability at high temperatures and high pHs.

The present inventors have continued an extensive search with a view toward finding microorganisms capable of producing a carboxymethylcellulase from the natural world. As a result, it has been found that microorganisms collected from the soil in The Philippines and belonging to the genus Bacillus produce new Carboxymethylcellulase 5430 or 5812, which is useful as an additive for laundry detergent compositions, and Carboxymethylcellulases 5430 and 5812 are broader in active pH range than the conventional carboxymethylcellulases, excellent in thermal stability and in particular, good in stability at high pH values, leading to completion of the present invention.

DISCLOSURE OF THE INVENTION

The present invention is directed to Carboxymethylcellulases 5430 and 5812 broad in active pH range and active temperature range, good in thermal stability and excellent in resistance to alkali.

The present invention is also concerned with microorganisms belonging to the genus Bacillus and producing said Carboxymethylcellulase 5430 or 5812.

BEST MODE FOR CARRYING OUT THE INVENTION

Microorganisms producing Carboxymethylcellulase 5430 or 5812 according to this invention show the following bacteriological properties. Incidentally, the following A through C are media used for isolating and incubating the enzyme-producing bacteria. Besides, $Na_2CO_3$ was sterilized separately from other components to add it.

Medium A (PCMC medium):
  polypeptone (product of Nippon Seiyaku K.K), 20 g; carboxymethylcellulose (CMC, product of Sanyo Kokusaku Pulp Co., Ltd.), 10 g; yeast extract (product of Difco Laboratories), 1 g; $KH_2PO_4$ (product of Wako Pure Chemical Industries, Ltd.), 1 g; NaCl (product of Merck), 5 g; $Na_2CO_3$ (anhydrous; product of Iwai Kagaku Co., Ltd.) 5 g; $MgSO_4 7H_2O$ (product of Wako Pure Chemical Industries, Ltd.), 0.2 g; Trypan blue dye (product of Merck), 0.075 g; agar (product of Difco Laboratories), 15 g (deionized water was added to prepare a 1.0–1 medium).

Medium B:
  Prepared in the same manner as in Medium A except for omission of Trypan blue dye.

Medium C (CMC-peptone medium):
  CMC, 10 g; polypeptone, 20 g; yeast extract, 0.5 g; $KH_2PO_4$, 1 g; NaCl, 5 g; $Na_2CO_3$, 5 g (deionized water was added to prepare a 1.0–medium).

Bacteriological Properties of Carboxymethylcellulase 5430-Producing Bacteria 1. Result of microscopic observation:
   The microorganisms are rods of 0.7–0.8 $\mu m \times$ 1.2–2.9 $\mu m$ in size, which form ellipsoidal spores (0.7–1.0 $\mu m \times$ 0.7–1.5 $\mu m$) on the center or subterminals thereof.
2. Motility: Positive, with peritrichous flagella.
3. Gram-staining: Positive.
4. Growth conditions in various media:
   (1) On nutrient agar plate medium:
     The shape of colony is circular. Its surface is rough, and the edge is undulate. The color of the colony is white.
   (2) In nutrient broth medium:
     Grown.
   (3) NaCl tolerance in nutrient broth:
     The bacteria grow in 5% and 7% NaCl, but do not grow in 10% NaCl.
   (4) On gelatin medium:
     Gelatin is liquefied.
   (5) In litmus milk medium:
     The upper layer of the culture medium is slightly decolored.
5. Physiological properties:
   (1) Reduction of nitrate to nitrite: Negative.
   (2) Denitrification: Negative.
   (3) MR test: Negative.
   (4) V-P test: Positive.
   (5) Formation of indol: Negative.
   (6) Formation of hydrogen sulfide: Positive.
   (7) Hydrolysis of starch: Negative.
   (8) Hydrolysis of casein: Positive.
   (9) Utilization of citrate:
     Simons citrate agar plate medium: Positive.
     Christensen citrate agar plate medium: Positive.
   (10) Utilization of inorganic nitrogen: Negative.
   (11) Formation of pigment:
     King A medium: Negative.
     King B medium: Negative.
     Potato Dextrose Agar Eiken: Negative.
     Mannitol-Salt Agar medium: Negative.
   1(12) Urease: Negative.
   (13) Oxidase: Positive.
   (14) Catalase: Positive.
   (15) Range of growth:
     Temperature for growth: 15°–50° C.
     Optimum temperature for growth: 25°–<50° C.
     pH for growth: 4.7–10
     Optimum pH for growth: 6.0–9.5
   (16) Requirement for Oxygen:
     Grown both aerobically and anaerobically.
   (17) O-F test: Fermented.
   (18) Utilization of propionate: Positive.
   (19) Degradation of tyrosine: Negative.
   (20) Deamination of phenylalanine: Negative.
   (21) Acid formation from sugars:
     Positive: D-ribose, L-arabinose, D-xylose, D-glucose, D-mannose, sucrose, trehalose, mannitol, glycerol, D-galactose, sorbitol.
     Negative: D-fructose, maltose, inositol, lactose, dextrin, raffinose, starch.
   (22) G+C content of DNA: 42.9 mol %.

Bacteriological Properties of Carboxymethylcellulase 5812-Producing Bacteria 1. Result of microscopic observation:
   The microorganisms are rods of 0.6–0.8 $\mu m \times$ 1.5–3.3 $\mu m$ in size, which form ellipsoidal spores (0.7–1.0 $\mu m \times$ 1.0–1.6 $\mu m$) on the center or subterminals thereof.
2. Motility: Positive, with peritrichous flagella.
3. Gram-staining: Positive.
4. Growth conditions in various media:
   (1) On nutrient agar plate medium:
     The shape of colony is circular. Its surface is rough, and the edge is undulate. The color of the colony is white or extremely pale yellow.
   (2) In nutrient broth medium:
     Grown.
   (3) NaCl tolerance in nutrient broth:
     The bacteria grow in 5% NaCl, but do not grow in 7% and 10% NaCl.
   (4) On gelatin medium:
     Gelatin is liquefied.
   (5) In Litmus milk medium:
     The upper layer of the culture medium is slightly decolored.
5. Physiological properties:
   (1) Reduction of nitrate to nitrite: Negative.
   (2) Denitrification: Negative.
   (3) MR test: Negative.
   (4) V-P test: Positive.
   (5) Formation of indol: Negative.
   (6) Formation of hydrogen sulfide: Positive.
   (7) Hydrolysis of starch: Negative.
   (8) Hydrolysis of casein: Positive.
   (9) Utilization of citrate:
     Simons citrate agar plate medium: Positive.
     Christensen citrate agar plate medium: Positive.
   (10) Utilization of inorganic nitrogen: Negative.
   (11) Formation of pigment:
     King A medium: Negative.
     King B medium: Negative.
     Potato Dextrose Agar Eiken: Negative.
     Mannitol-Salt Agar medium: Negative.

(12) Urease: Negative.
(13) Oxidase: Positive.
(14) Catalase: Positive.
(15) Range of growth:
   Temperature for growth: 15°–45° C.
   Optimum temperature for growth: 25°–<45° C.
   pH for growth: 4.7–10
   Optimum pH for growth: 6.0–9.5
(16) Requirement for Oxygen:
   Grown both aerobically and anaerobically.
(17) O-F test: Fermented.
(18) Utilization of propionate: Positive.
(19) Degradation of tyrosine: Negative.
(20) Deamination of phenylalanine: Negative.
(21) Acid formation from sugars:
   Positive: D-ribose, L-arabinose, D-xylose, D-glucose, mannitol.
   Negative: D-mannose, D-fructose, maltose, sucrose, trehalose, inositol, glycerol, D-galactose, lactose, sorbitol, dextrin, raffinose, starch.
(22) G+C content of DNA: 42.6 mol %.

The above-described bacteriological properties were referred to Bergey's Manual of Systematic Bacteriology, Vol. 2. As a result, these strains were judged to be species of the genus Bacillus, which were rods with spore.

Since the bacteriological properties of these strains differed from those of any known Bacillus species, these strains were judged to be new strains, named "Bacillus sp. PKM-5430" and "Bacillus sp. PKM-5812", and deposited with the Fermentation Research Institute, Agency of Industrial Science and Technology as International Deposition Nos. BP-4087 and BP-4088, respectively.

In order to collect Carboxymethylcellulase 5430 or 5812 according to this invention, it is only necessary to incubate the above-described Bacillus sp. PKM-5430 or PKM-5812 or a variant thereof in a medium, and isolate and purify the resulting culture by the conventionally-known purification method for enzyme.

Upon the fermentative production of Carboxymethylcellulase 5430, it is only necessary to sterilize a suitable medium by heating or the like and then inoculate Bacillus sp. PKM-5430 (International Deposition No. BP-4087) into the medium to subject it to shaking culture or aerobic spinner culture for 1–4 days at 15°–50° C., preferably 25°–45° C. The adjustment of pH to neutrality to 10 gives good results. Although foaming may occur in some cases, this problem is solved by suitably adding an appropriate antifoam to the medium.

Upon the fermentative production of Carboxymethylcellulase 5812 on the other hand, it is only necessary to sterilize a suitable medium by heating or the like and then inoculate Bacillus sp. PKM-5812 (International Deposition No. BP-4088) into the medium to subject it to shaking culture or aerobic spinner culture for 1–4 days at 15°–45° C., preferably 25°–43° C. The adjustment of pH to weak acidity (pH: about 5) to 10 gives good results. Although foaming may occur in some cases, this problem is solved by suitably adding an appropriate antifoam to the medium.

Carboxymethylcellulase 5430 or 5812 may be produced by incorporating assimilable nitrogen source and carbon source in suitable combination into a culture medium. No particular limitation is imposed on both nutrient sources. As exemplary nitrogen sources, may be mentioned organic nitrogen sources such as corn gluten meal, soybean powder, corn steep liquor, casamino acids, yeast extract, Pharmamedia, sardine meal, meat extract, peptone, Hipro, Ajipower, coffee cake, cottonseed cake, Cultivator, Amiflex, Ajipron, Zest and Ajix. As illustrative carbon sources, may be mentioned chaff, wheat-gluten bread, vegetable fibrous materials such as filter paper and sawdust, blackstrap molasses, invert sugar, CMC, Avicel, cellulose cotton, xylan, pectin, and in addition, assimilable carbon sources, for example, ribose, arabinose, xylose, glucose, mannose, fructose, maltose, sucrose, mannitol, inositol and glycerol, and assimilable organic acids, for example, acetic acid and citric acid. Namely, any medium obtained by suitably combining these nitrogen sources and carbon sources with each other may be used. The above-mentioned nutrient sources are not particularly limited. In addition, media containing phosphoric acid, inorganic salts such as $Mg^{2+}$, $Ca^{2+}$, $Mn^{2+}$, $Zn^{2+}$, $Ca^{2+}$, $Na^+$ and $K^+$ and optionally inorganic and organic minor nutrient sources may be suitably chosen for use.

In order to obtain Carboxymethylcellulase 5430 or 5812 from the thus-obtained culture, the general collection and purification means may be followed. Namely, the culture is centrifuged or filtered to separate the strain from the culture. The supernatant of the culture are treated by the conventional separation means, for example, the salting out, isoelectric precipitation or solvent precipitation (methanol, ethanol, isopropanol, etc.), to precipitate proteins, or concentrated by ultrafiltration, thereby obtaining a crude enzyme solution of Carboxymethylcellulase 5430 or 5812. After precipitating the enzyme in, for example, ammonium sulfate (30–100% saturated fraction) for the salting out, or in, for example, 75% ethanol for the solvent precipitation, the precipitate may be filtered or centrifuged and desalted to form lyophilized powder. As a method for the desalting, is used a general method such as dialysis or gel filtration on Sephadex or Bio-Gel.

Although the crude enzyme solution may be used as it is, as necessary, it may also be purified by the conventionally-known method, for example, the suitable combination of chromatography on hydroxyapatite, ion-exchange chromatography on DEAE-Sephadex or DEAE-Bio-Gel and gel filtration chromatography on Sephadex or Bio-Gel to use it as a purified enzyme.

The thus-obtained Carboxymethylcellulases 5430 and 5812 (crude enzymes) have such properties as described below. Incidentally, the determination of enzymatic activities was conducted in accordance with the following methods.

(a) Carboxymethylcellulase activity:

Activities were determined by the DNS method (J. R. Summer and G. F. Somers, Laboratory Experiments in Biological Chemistry, Academic Press, New York, U.S.A., 1944). Namely, 0.1 ml of a suitably diluted enzyme solution was added to 0.9 ml of a 1.1% (w/v) solution of a CMC (A01MC) substrate in 0.1M glycine-NaOH buffer (pH: 9.0). After a 20-minute reaction at 40° C., 1 ml of 0.05% (w/v) 3,5-dinitrosalicylic acid solution (product of Wako Pure Chemical Industries, Ltd.) was added, and the resulting mixture was immediately placed in a boiling water bath for 5 minutes, followed by cooling in an iced water bath. Then, 4 ml of deionized water was added further, afterwhich, colorimetry was conducted by measuring an absorbance at 535 nm. With respect to enzymatic activity, the amount of enzyme, which liberates reducing sugars corresponding to 1 μmole of glucose for 1 minute, was defined as 1 unit.

(b) Hydrolytic activities toward cellulosic substrates:

Sodium hydroxide- and phosphoric acid-swollen celluloses were prepared according to the method of Tomita et al. [Y. Tomita, H. Suzuki and K. Nisizawa, *J. Biochem.*, 78, 499(1975)]. The reducing sugar liberated was determined in a similar manner to that of the method (a) except that substrate solutions containing cellulose substrates were used, and the reaction was conducted at 30° C.

(c) Hydrolytic activities toward polysaccharides:

The reducing sugar liberated was determined in a similar manner to that of the method (a) except that substrate solutions containing polysaccharides were used, and the reaction was conducted at 30° C.

(d) Hydrolytic activities toward p-nitrophenyl-β-D-glucopyranoside (PNPG; product of Sigma Chemical) and p-nitrophenyl-β-D-cellobioside (PNPC; product of Sigma Chemical):

A suitably diluted enzyme solution was added to a solution of 8 mM of a PNPG or PNPC substrate in 0.1M phosphate buffer of pH 7.0 to react them for 20 minutes at 30° C. The p-nitrophenol liberated was determined at 400 nm and the amount formed was calculated.

Enzymological Properties of Carboxymethylcellulase 5430

(1) Action:

This enzyme has an enzymatic activity toward CMC.

(2) Substrate specificity:

As shown in the following Table 1, this enzyme shows strong activity toward CMC and lichenan. The enzyme is also active toward cellobiose, PNPG, PNPC, cellulose powder and phosphoric acid-swollen cellulose.

TABLE 1

| Substrate | Concentration of substrate | Relative activity (%) |
|---|---|---|
| CMC*[1] | 1.0% | 100.0 |
| Avicel | 1.0% | 0.0 |
| Cellulose Powder (Sigmacell 20) | 1.0% | 0.1 |
| Cellulose Powder (Sigmacell 100) | 1.0% | 1.1 |
| Phosphoric acid-swollen cellulose | 1.0% | 7.3 |
| Sodium hydroxide-swollen cellulose | 1.0% | 0.0 |
| Curdlan*[2] | 1.0% | 0.0 |
| Laminarin*[3] | 1.0% | 1.1 |
| Lichenan*[4] | 1.0% | 78.7 |
| Cellobiose | 0.1% | 0.4 |
| PNPC | 8 mM | 1.0 |
| PNPG | 8 mM | 0.8 |

*[1]: The activity toward CMC at 30° C. was taken as 100% to determine relative activities toward other substrates.
*[2]: Derived from *Alcaligenes faecalis* var. *myxogenes*; product of Wako Pure Chemical Industries, Ltd.
*[3]: Derived from *Laminaria digitata*; product of Sigma Chemical.
*[4]: Derived from *Cetraria islandica*; product of Sigma Chemical.

Figure 1:
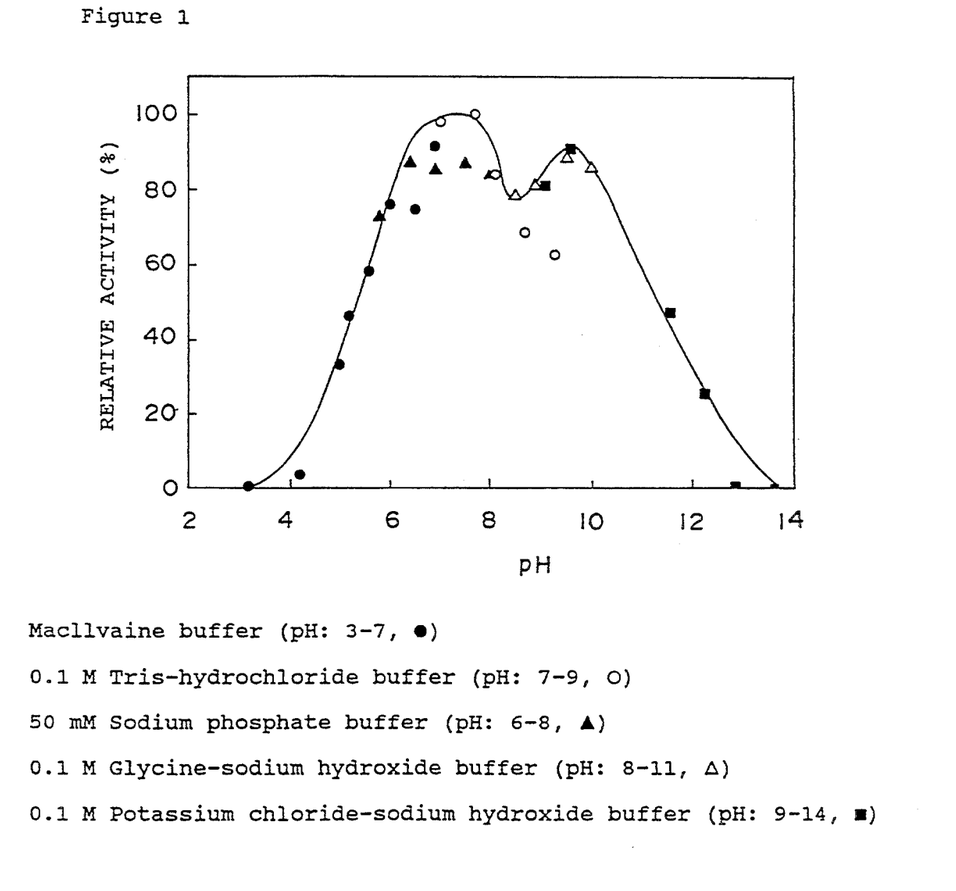
FIGS. 1, 2, 3 and 4 illustrate a pH-activity curve of Carboxymethylcellulase 5430, a pH stability curve of Carboxymethylcellulase 5430, a temperature-activity curve of Carboxymethylcellulase 5430 and a temperature stability of Carboxymethylcellulase 5430, respectively.

(3) Active pH range and optimum pH:

This enzyme is active in a pH range of 4.2–12.5 and has two optimum pH values of about 7.7 and about 9.5 (FIG. 1). Even at pH 10, about 90% of the maximum activity is shown, while at pH 11.5, the activity is still higher than about 50%. Even at pH 12.5, about 20% of the activity is maintained.

Figure 2:
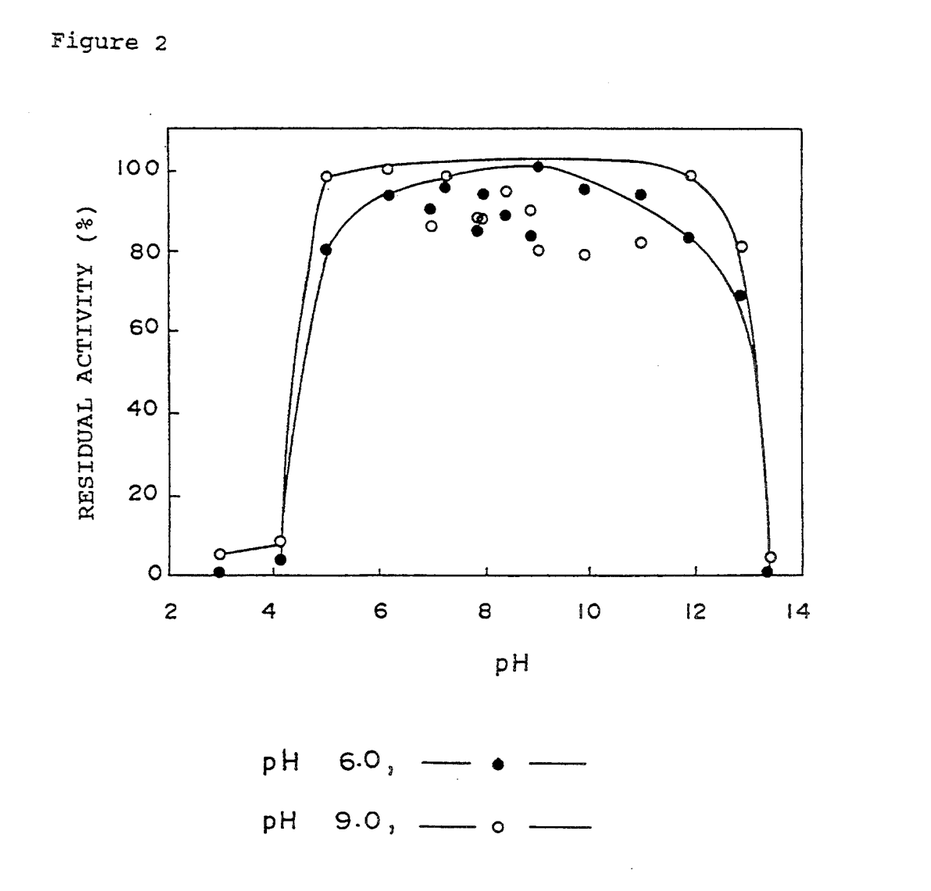

(4) pH Stability:

The stability of the enzyme to pH was investigated by overnight treatment at 5° C. in MacIlvaine buffer (pH: 3–7), 0.1M tris-hydrochloride buffer (pH: 7–9), 0.1M glycine-sodium hydroxide buffer (pH: 8–11) and 0.1M potassium chloride-sodium hydroxide buffer (pH: 9–14) and then measurement of residual activities in 0.1M sodium phosphate buffer of pH 6.0 and 0.1M glycine-sodium hydroxide buffer of pH 9.0. As a result, the enzyme is extremely stable over a pH range of 4.6–12.8 on both pHs (FIG. 2).

Figure 3:
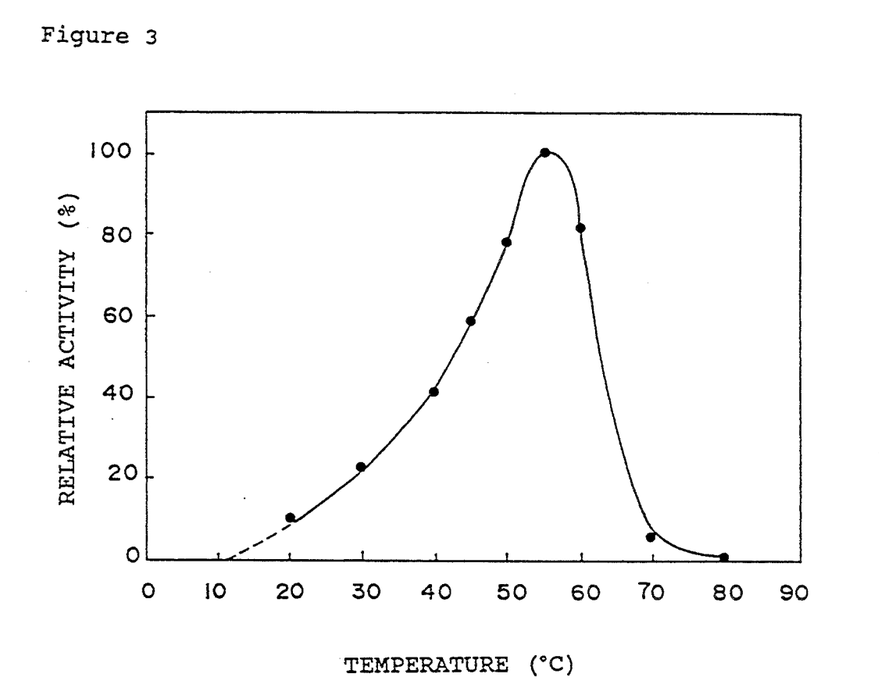

(5) Active temperature range and optimum temperature:

The carboxymethylcellulase activity of this enzyme was measured in 0.1M glycine-sodium hydroxide buffer of pH 9.0. The enzyme is active over a wide temperature range of 10°–78° C., and its optimum temperature is observed at about 55° C. (FIG. 3).

Figure 4:
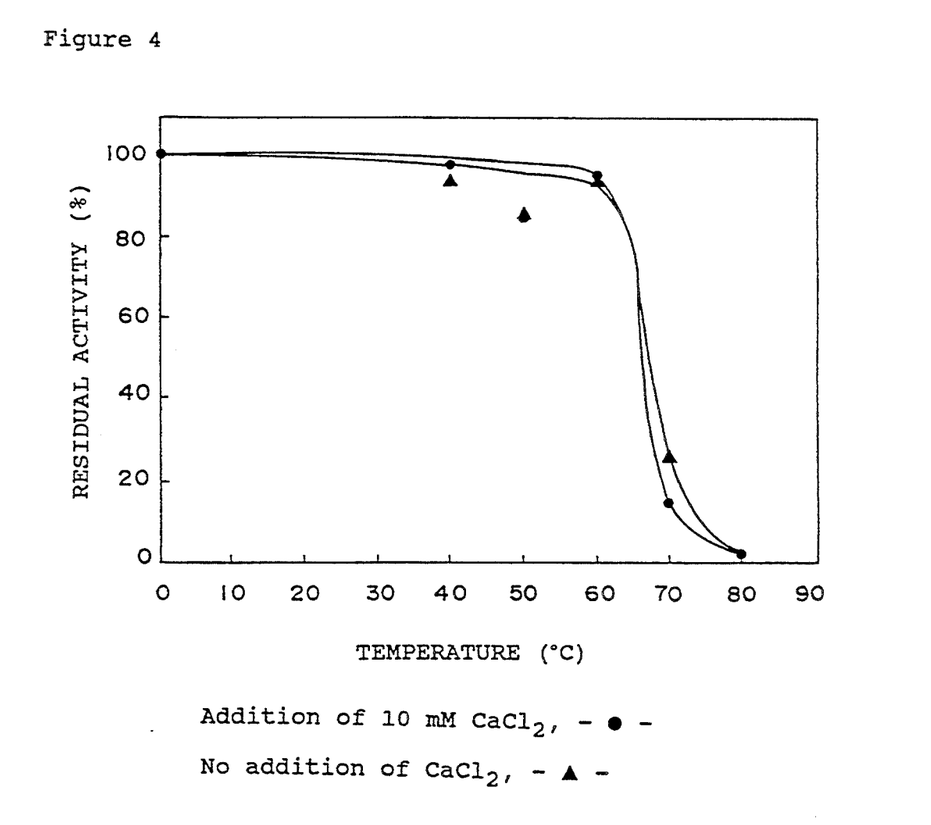

(6) Thermal stability:

After pretreating this enzyme for 10 minutes at various temperatures, its residual activity was determined in 0.1M glycine-sodium hydroxide buffer of pH 9.0 to investigate the thermal stability thereof. As a result, it was found that the enzyme was scarcely deactivated after heated to 60° C., and still retained some activity even after heated to 80° C. (FIG. 4). The addition of $Ca^{2+}$ brought about no effect under the above conditions.

(7) Effects of metal ions:

Each metal ion preparation shown in Table 2 and CMC were mixed with the enzyme solution and the carboxymethylcellulase activity of the enzyme was measured for 20 minutes at 40° C. in 0.1M glycine-sodium hydroxide buffer of pH 9.0. Among the various metal ions tested, $Hg^{2+}$, at 1 mM, inhibited the activity of the enzyme by about 75%. On the contrary, $Co^{+2}$, at 1 mM stimulated the activity of the enzyme by about 30% and $Mn^{+2}$, at 1 mM, also stimulated the activity by about 50%. The other metal ions shown in Table 2 showed moderate levels of either inhibition or stimulation and metal ions other than the above showed no effect at all.

TABLE 2

| Metal ions | Concentration (mM) | Relative activity (%) |
|---|---|---|
| None | — | 100 |
| $Ca^{2+}$ | 1 | 108 |
| $Mg^{2+}$ | 1 | 108 |
| $Mn^{2+}$ | 1 | 130 |
| $Co^{2+}$ | 1 | 149 |
| $Pb^{2+}$ | 1 | 81 |
| $Zn^{2+}$ | 1 | 92 |
| $Hg^{2+}$ | 1 | 25 |
| $Cu^{2+}$ | 1 | 97 |
| $Fe^{2+}$ | 1 | 105 |
| $Fe^{3+}$ | 1 | 110 |
| $Al^{3+}$ | 1 | 101 |
| $Na^+$ | 50 | 121 |
| $K^+$ | 50 | 116 |

(8) Effects of surfactants:

Surfactants shown in Table 3 were separately mixed with the enzyme solution to measure the carboxymethylcellulase activity of the enzyme for 20 minutes at 40° C. in 0.1M glycine-sodium hydroxide buffer of pH 9.0. As apparent from Table 3, the activity of this enzyme was either scarcely inhibited or stimulated by sodium dodecyl sulfate (SDS), sodium linear alkylbenzenesulfonate (LAS), sodium alkyl sulfate (AS), sodium polyoxyethylene alkyl sulfate (ES), sodium α-olefin sulfonate (AOS), sodium α-sulfonated fatty acid ester (α-SFE), fatty acid salt (soap) or polyoxyethylene alkyl ether. In particular, SDS and the fatty acid salt stimulated the activity of the enzyme by 26% and 45%, respectively.

TABLE 3

| Surfactants | Concentration (%) | Relative activity (%) |
|---|---|---|
| None | — | 100 |
| SDS | 0.05 | 126 |
| LAS | 0.05 | 105 |
| AS | 0.05 | 123 |
| ES | 0.05 | 102 |
| AOS | 0.05 | 107 |
| α-SFE | 0.05 | 116 |
| Fatty acid salt (soap) | 0.05 | 145 |
| Softanol 70H | 0.05 | 107 |

(9) Effects of inhibitors:

Inhibitors shown in Table 4 were separately mixed with the enzyme solution to measure the carboxymethylcellulase activity of the enzyme for 20 minutes at 40° C. in 0.1M glycine-sodium hydroxide buffer of pH 9.0. N-Bromosuccinimide drastically inhibited the activity of this enzyme by 97%, while phenylmethanesulfonyl fluoride moderately inhibited the enzyme by 24%. However, the activity of the enzyme was not inhibited by the other inhibitors.

TABLE 4

| Inhibitors | Concentration (mM) | Relative activity (%) |
|---|---|---|
| None | — | 100 |
| N-Bromo-* succinimide | 0.1 | 4 |
| Sodium azide | 1.0 | 118 |
| Hydroxylamine hydrochloride | 1.0 | 133 |
| Monoiodo acetic acid | 1.0 | 117 |
| 4-Chloromercuribenzoic acid | 1.0 | 118 |
| Phenylmethanesulfonyl fluoride | 1.0 | 76 |

*: The enzyme was pretreated at pH 5.5 (50 mM acetate buffer).

(10) Effects of chelating agents, thiol reagents, additives and proteinases:

Reagents shown in Table 5 were separately mixed with the enzyme solution to measure the carboxymethylcellulase activity of the enzyme for 20 minutes at 40° C. in 0.1M glycine-sodium hydroxide buffer of pH 9.0. The activity of this enzyme was somewhat inhibited by EDTA or EGTA. On the other hand, 2-mercaptoethanol and dithiothreitol, each added at 1 mM, stimulated the activity of the enzyme by 39% and 50%, respectively. It was not observed that the proteinases such as alkalase, maxatase, savinase and Protease API-21 inactivated the enzyme of this invention under this reaction conditions.

TABLE 5

| Reagents | Concentration | Relative activity (%) |
|---|---|---|
| None | — | 100 |
| Zeolite | 0.05% | 99 |
| EDTA | 1 mM | 71 |
| EGTA | 1 mM | 66 |
| o-Phenanthroline | 1 mM | 98 |
| 2-Mercaptoethanol | 1 mM | 139 |
| Dithiothreitol | 1 mM | 150 |
| Alkalase | 0.01% | 111 |
| Maxatase | 0.01% | 105 |
| Savinase | 0.01% | 107 |

TABLE 5-continued

| Reagents | Concentration | Relative activity (%) |
|---|---|---|
| Protease API-21 | 0.01% | 123 |

(11) Molecular weight:

The molecular weight of this enzyme was estimated by gel filtration on Bio-Gel A 0.5 m in accordance with the method of Shikata and Nisizawa [S. Shikata and K. Nisizawa, *J. Biochem.*, 78, 499(1975)] and found to be about 26,000±1,000.

Enzymological Properties of Carboxymethylcellulase 5812

(1) Action:

This enzyme has an enzymatic activity toward CMC.

(2) Substrate specificity:

As shown in the following Table 6, this enzyme shows strong activity toward CMC and lichenan. The enzyme is also active toward cellobiose, PNPG, PNPC, cellulose powder and phosphoric acid-swollen cellulose.

TABLE 6

| Substrate | Concentration of substrate | Relative activity (%) |
|---|---|---|
| CMC*1 | 1.0% | 100.0 |
| Avicel | 1.0% | 0.0 |
| Cellulose Powder (Sigmacell 20) | 1.0% | 0.1 |
| Cellulose Powder (Sigmacell 100) | 1.0% | 1.0 |
| Phosphoric acid-swollen cellulose | 1.0% | 7.5 |
| Sodium hydroxide-swollen cellulose | 1.0% | 0.0 |
| Curdlan*2 | 1.0% | 0.0 |
| Laminarin*3 | 1.0% | 1.0 |
| Lichenan*4 | 1.0% | 71.2 |
| Cellobiose | 0.1% | 0.4 |
| PNPC | 8 mM | 0.6 |
| PNPG | 8 mM | 0.2 |

*1: The activity toward CMC at 30° C. was taken as 100% to determine relative activities toward other substrates.
*2: Derived from *Alcaligenes faecalis* var. *myxogenes*; product of Wako Pure Chemical Industries, Ltd.
*3: Derived from *Laminaria digitata*; product of Sigma Chemical.
*4: Derived from *Cetraria islandica*; product of Sigma Chemical.

Figure 5:
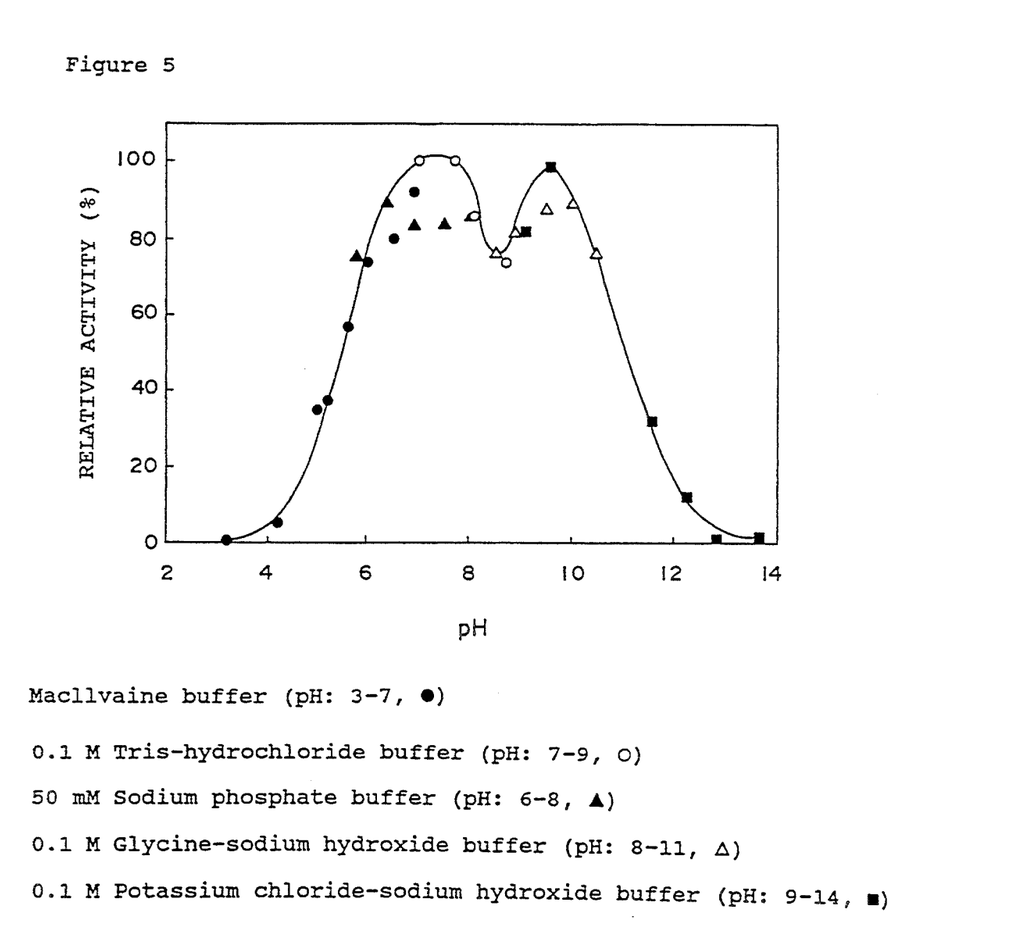
FIGS. 5, 6, 7 and 8 illustrate a pH-activity curve of Carboxymethylcellulase 5812, a pH stability curve of Carboxymethylcellulase 5812, a temperature-activity curve of Carboxymethylcellulase 5812 and a temperature stability of Carboxymethylcellulase 5812, respectively.

(3) Active pH range and optimum pH:

This enzyme is active in a pH range of 4.2–12.5 and has two optimum pH values of about 7.7 and about 9.5 (FIG. 5). Even at pH 10, about 90% of the maximum activity is shown, while at pH 11.5, the activity is still higher than about 30%. Even at pH 12.5, about 10% of the activity is maintained.

Figure 6:
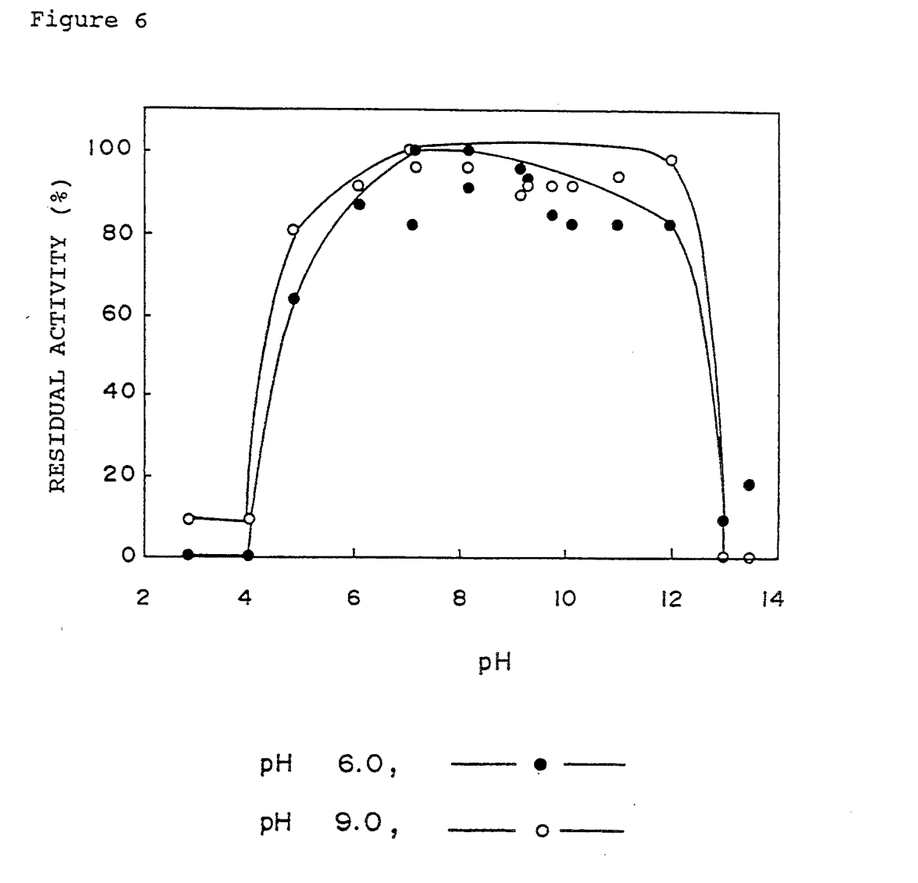

(4) pH Stability:

The stability of the enzyme to pH was investigated by overnight treatment at 5° C. in MacIlvaine buffer (pH: 3–7), 0.1M tris-hydrochloride buffer (pH: 7–9), 0.1M glycine-sodium hydroxide buffer (pH: 8–11) and 0.1M potassium chloride-sodium hydroxide buffer (pH: 9–14) and then measurement of residual activities in 0.1M sodium phosphate buffer of pH 6.0 and 0.1M glycine-sodium hydroxide buffer of pH 9.0. As a result, the enzyme is extremely stable over a pH range of 4.8–12 on both pHs (FIG. 6).

Figure 7:
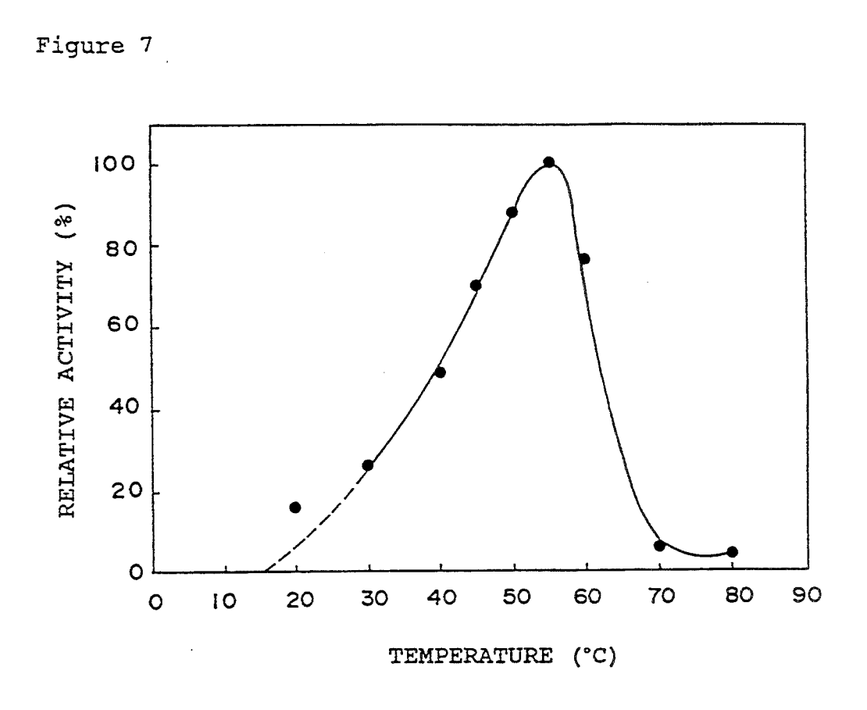

(5) Active temperature range and optimum temperature:

The carboxymethylcellulase activity of this enzyme was measured in 0.1M glycine-sodium hydroxide buffer of pH 9.0. The enzyme is active over a wide temperature range of 10°–70° C., and its optimum temperature is observed at about 55° C. (FIG. 7).

Figure 8:
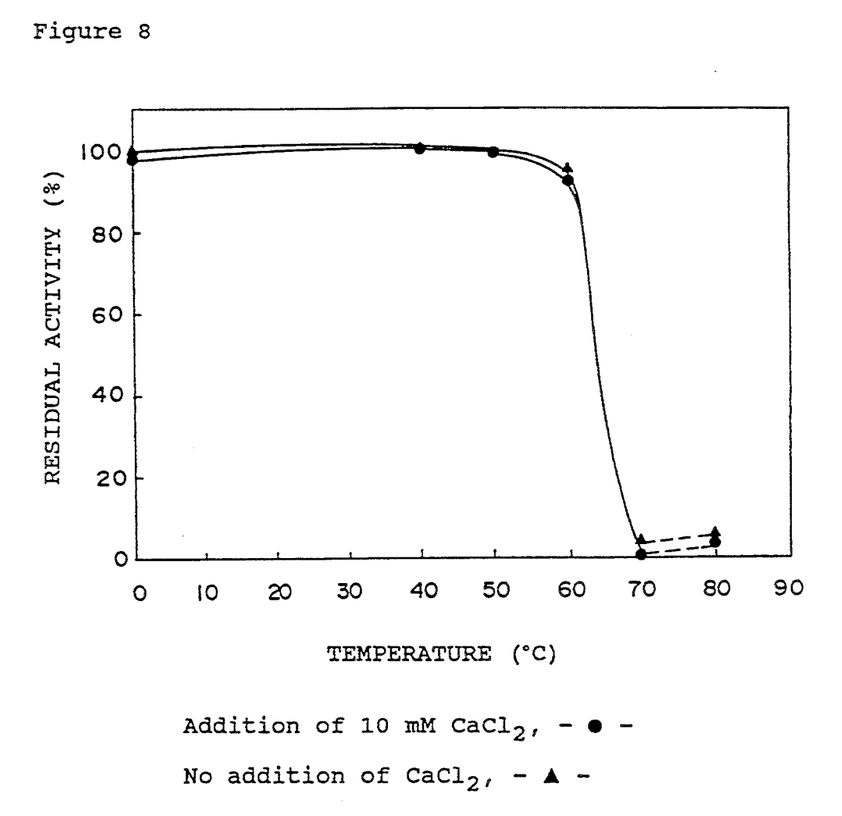

(6) Thermal stability:

After pretreating this enzyme for 10 minutes at various temperatures, its residual activity was determined in 0.1M glycine-sodium hydroxide buffer of pH 9.0 to investigate the thermal stability thereof. As a result, it was found that the enzyme was scarcely deactivated after heated to 60° C., and still retained some activity even after heated to 70° C. (FIG. 8). The addition of $Ca^{2+}$ brought about no effect under the above conditions.

(7) Effects of metal ions:

Each metal ion preparation shown in Table 7 and CMC were mixed with the enzyme solution and the carboxymethylcellulase activity of the enzyme was measured for 20 minutes at 40° C. in 0.1M glycine-sodium hydroxide buffer of pH 9.0. Among the various metal ions tested, $Hg^{2+}$, at 1 mM, inhibited the activity of the enzyme by about 75%. On the contrary, $Co^{+2}$, at 1 mM stimulated the activity of the enzyme by about 50%, and $Mn^{+2}$, at 1 mM, also stimulated the activity by 53%. The other metal ions shown in Table 7 showed moderate levels of either inhibition or stimulation and metal ions other than the above showed no effect at all.

TABLE 7

| Metal ions | Concentration (mM) | Relative activity (%) |
|---|---|---|
| None | — | 100 |
| $Ca^{2+}$ | 1 | 108 |
| $Mg^{2+}$ | 1 | 109 |
| $Mn^{2+}$ | 1 | 153 |
| $Co^{2+}$ | 1 | 150 |
| $Pb^{2+}$ | 1 | 93 |
| $Zn^{2+}$ | 1 | 96 |
| $Hg^{2+}$ | 1 | 27 |
| $Cu^{2+}$ | 1 | 98 |
| $Fe^{2+}$ | 1 | 101 |
| $Fe^{3+}$ | 1 | 104 |
| $Al^{3+}$ | 1 | 97 |
| $Na^+$ | 50 | 120 |
| $K^+$ | 50 | 126 |

(8) Effects of surfactants:

Surfactants shown in Table 8 were separately mixed with the enzyme solution to measure the carboxymethylcellulase activity of the enzyme for 20 minutes at 40° C. in 0.1M glycine-sodium hydroxide buffer of pH 9.0. As apparent from Table 8, the activity of this enzyme was either scarcely inhibited or stimulated by sodium dodecyl sulfate (SDS), sodium linear alkylbenzenesulfonate (LAS), sodium alkyl sulfate (AS), sodium polyoxyethylene alkyl sulfate (ES), sodium α-olefin sulfonate (AOS), sodium α-sulfonated fatty acid ester (α-SFE), fatty acid salt (soap) or polyoxyethylene alkyl ether. In particular, SDS and the fatty acid salt stimulated the activity of the enzyme by 21% and 23%, respectively.

TABLE 8

| Surfactants | Concentration (%) | Relative activity (%) |
|---|---|---|
| None | — | 100 |
| SDS | 0.05 | 121 |
| LAS | 0.05 | 96 |
| AS | 0.05 | 112 |
| ES | 0.05 | 112 |
| AOS | 0.05 | 105 |
| α-SFE | 0.05 | 97 |

TABLE 8-continued

| Surfactants | Concentration (%) | Relative activity (%) |
|---|---|---|
| Fatty acid salt (soap) | 0.05 | 123 |
| Softanol 70H | 0.05 | 116 |

(9) Effects of inhibitors:

Inhibitors shown in Table 9 were separately mixed with the enzyme solution to measure the carboxymethylcellulase activity of the enzyme for 20 minutes at 40° C. in 0.1M glycine-sodium hydroxide buffer of pH 9.0. N-Bromosuccinimide drastically inhibited the activity of this enzyme by 97%. However, the activity of the enzyme was not inhibited by the other inhibitors.

TABLE 9

| Inhibitors | Concentration (mM) | Relative activity (%) |
|---|---|---|
| None | — | 100 |
| N-Bromo-*succinimide | 0.1 | 3 |
| Sodium azide | 1.0 | 117 |
| Hydroxylamine hydrochloride | 1.0 | 123 |
| Monoiodo acetic acid | 1.0 | 104 |
| 4-Chloromercuri-benzoic acid | 1.0 | 105 |
| Phenylmethane-sulfonyl fluoride | 1.0 | 107 |

*: The enzyme was pretreated at pH 5.5 (50 mM acetate buffer).

(10) Effects of chelating agents, thiol reagents, additives and proteinases:

Reagents shown in Table 10 were separately mixed with the enzyme solution to measure the carboxymethylcellulase activity of the enzyme for 20 minutes at 40° C. in 0.1M glycine-sodium hydroxide buffer of pH 9.0. The activity of this enzyme was somewhat inhibited by EDTA or EGTA. On the other hand, 2-mercaptoethanol and dithiothreitol, each added at 1 mM, stimulated the activity of the enzyme by 52% and 84%, respectively. It was not observed that the proteinases such as alkalase, maxatase, savinase and Protease API-21 inactivated the enzyme of this invention under this reaction conditions.

TABLE 10

| Reagents | Concentration | Relative activity (%) |
|---|---|---|
| None | — | 100 |
| Zeolite | 0.05% | 100 |
| EDTA | 1 mM | 79 |
| EGTA | 1 mM | 73 |
| o-Phenanthroline | 1 mM | 100 |
| 2-Mercaptoethanol | 1 mM | 152 |
| Dithiothreitol | 1 mM | 184 |
| Alcalase | 0.01% | 107 |
| Maxatase | 0.01% | 109 |
| Savinase | 0.01% | 106 |
| Protease API-21 | 0.01% | 110 |

(11) Molecular weight:

The molecular weight of this enzyme was estimated by gel filtration on Bio-Gel A 0.5 m in accordance with the method of Shikata and Nisizawa [S. Shikata and K. Nisizawa, *J. Biochem.*, 78, 499(1975)] and found to be about 26,000±1,000.

As described above, Carboxymethylcellulase 5430 features that it is active over a very broad pH range of 4.2–12.5 and extremely stable at any pH up to 12.8, and moreover that it is active over a broad temperature range of 10°–78° C., good in thermal stability and has the potential for application to detergents formulated for high temperature washing and/or alkaline detergents. Also, Carboxymethylcellulase 5812 features that it is active over a very broad pH range of 4.2–12.5 and extremely stable at any pH up to 12, and moreover that it is active over a broad temperature range of 10°–70° C., good in thermal stability and has the potential for application to detergents formulated for high temperature washing and/or alkaline detergents.

Further, the activities of these Carboxymethylcellulases 5430 and 5812 are scarcely inhibited even by formulation ingredients for detergents, such as surfactants, metal ions and proteinases.

EXAMPLES

The present invention will hereinafter be described more specifically by the following examples.

Example 1

About 0.5 g of a soil sample, which had been collected in Davao City, Davao der Sur, The Philippines, was suspended in 9 ml of a sterile physiological saline solution and heated for 10 minutes at 80° C. The thus-heat-treated soil sample was suitably diluted, spread on an agar plate [PCMC medium (Medium A)] and then incubated for 3 days at 30° C. After the incubation, colonies with clear zones were spread on the same agar plate to incubate them for 3 days at 30° C., thereby forming colonies again.

Bacillus sp. PKM-5430 (International Deposition No. BP-4087) according to this invention was obtained in accordance with the above-described procedure.

Example 2

A portion of Bacillus sp. PKM-5430 obtained in Example 1 was subjected to slant culture using Medium B (prepared in the same manner as in Medium A except for omission of Trypan blue dye). Colonies thus obtained were then inoculated into 5 ml of a CMC-peptone medium (Medium C) contained in a 50-ml test tube and incubated for 2 days at 30° C. while shaking at 300 rpm. A 1-ml portion of the above culture was further inoculated into the 50-ml portion of the Medium C contained in a 500-ml Sakaguchi flask and incubated for 3 days at 30° C. while shaking at 120 rpm.

Cells were removed from the culture medium thus obtained by centrifugation to obtain a supernatant containing Carboxymethylcellulase 5430.

Example 3

The supernatant obtained in Example 2 was treated with ammonium sulfate (pH was kept neutral with dilute aqueous ammonia), and proteins which precipitated at 90% saturation were collected by centrifugation (11,000×g). The precipitate was dissolved in 20 mM phosphate buffer of pH 7.0, and dialyzed overnight at 5° C. against the same buffer.

The concentration of the proteins was determined by means of a Bio-Rad protein assay kit (product of Bio-Rad Laboratories) making use of bovine plasma gamma globulin as a standard in accordance with the method of Bradford [M. Bradford, *Anal. Biochem.*, 72, 248(1976)], whereby a crude enzyme solution having a specific activity of 3.47 unit (U)/mg of protein was found to be obtained.

Example 4

With respect to the crude enzyme solution obtained in Example 3, polyacrylamide gel electrophoresis (PAGE) was carried out on 9% (w/v) polyacrylamide slab gel (70 mm×80 mm, 1.0 mm thickness) making use of 150 mM tris-glycine buffer (pH: 8.8) as a running buffer in accordance with the method of Davis [B. J. Davis, *Ann. N. Y. Acad. Sci.*, 121, 404(1964)]. The electrophoresis was performed at 10 mA per gel for about 2 hours at room temperature. The proteins were then visualized by silver staining (kit of silver stain, product of Kanto Chemical Co., Inc.) in accordance with the method of Oakley et al. [B. R. Oakley, D. R. Kirsch and N. R. Morris, *Anal. Biochem.*, 105, 361(1980)].

Protein bands associated with carboxymethylcellulase activity were then visualized by active staining with Congo red. Namely, the slab gel after PAGE was placed on the surface of a CMC-agar plate and left over for 30 minutes at 37° C. in accordance with the method of Beguin [P. Beguin, *Anal. Biochem.*, 131, 333(1983)]. The CMC-agar plate was composed of 2% (w/v) of CMC (Sunrose A10MC), 3% (w/v) of NaCl, 10% (v/v) of 0.5M glycine-sodium hydroxide buffer (pH: 9.0) and 0.8% (w/v) of agar (product of Difco). This agar plate was stained with a 0.1% (w/v) Congo red (product of Wako Pure Chemical Industries, Ltd.) solution for 15 minutes at room temperature and then destained with a 1.0M NaCl solution for 15 minutes. As a result, a protein band having carboxymethylcellulase activity was detected at a position of 0.45 in terms of relative mobility (Rm).

Example 5

With respect to the crude enzyme solution obtained in Example 3, the isoelectric point (pI) was determined by PAGE in accordance with the method of Wringley [C. W. Wringley, *Methods Enzymol.*, 22, 559(1971)]. One hundred microliter of each enzyme solution (1 mg/ml) was electrophoresed in a 5% (w/v) acrylamide gel column containing 13.3 (w/v) of glycerol and 6.3% (v/v) of Pharmalyte (product of Pharmacia; pH range: 3–10) at a constant voltage of 200 V for about 15 hours. The cathode and anode were connected to an upper chamber (20 mM $H_3PO_4$) and a lower chamber (0.1M sodium hydroxide), respectively. After PAGE, the proteins were visualized by staining with 0.2% (w/v) Coomassie brilliant blue R-250 (product of Merck). Protein bands associated with carboxymethylcellulase activity were visualized by active staining in the same manner as in Example 4 to measure the relative mobility of an active band and to determine a pI value from a standard curve of known proteins. As a result, it was found to be pH 4.5.

Example 6

About 0.5 g of a soil sample, which had been collected in Los Baños, Laguna, The Philippines, was suspended in 9 ml of a sterile physiological saline solution and heated for 10 minutes at 80° C. The thus-heat-treated soil sample was suitably diluted, spread on an agar plate [PCMC medium (Medium A)] and then incubated for 3 days at 30° C. After the incubation, colonies with clear zones were spread on the same agar plate to incubate them for 3 days at 30° C., thereby forming colonies again.

Bacillus sp. PKM-5812 (International Deposition No. BP-4088) according to this invention was obtained in accordance with the above-described procedure.

Example 7

A portion of Bacillus sp. PKM-5812 obtained in Example 6 was subjected to slant culture using Medium B (prepared in the same manner as in Medium A except for omission of Trypan blue dye). Colonies thus obtained were then inoculated into 5 ml of a CMC-peptone medium (Medium C) contained in a 50-ml test tube and incubated for 2 days at 30° C. while shaking at 300 rpm. A 1-ml portion of the above culture was further inoculated into the 50-ml portion of the Medium C contained in a 500-ml Sakaguchi flask and incubated for 3 days at 30° C. while shaking at 120 rpm.

Cells were removed from the culture medium thus obtained by centrifugation to obtain a supernatant containing Carboxymethylcellulase 5812.

Example 8

The supernatant obtained in Example 7 was treated with ammonium sulfate (pH was kept neutral with dilute aqueous ammonia), and proteins which precipitated at 90% saturation were collected by centrifugation (11,000×g). The precipitate was dissolved in 20 mM phosphate buffer of pH 7.0, and dialyzed overnight at 5° C. against the same buffer.

The concentration of the proteins was determined by means of a Bio-Rad protein assay kit (product of Bio-Rad Laboratories) making use of bovine plasma gamma globulin as a standard in accordance with the method of Bradford [M. Bradford, *Anal. Biochem.*, 72, 248(1976)], whereby a crude enzyme solution having a specific activity of 7.73 unit (U)/mg of protein was found to be obtained.

Example 9

With respect to the crude enzyme solution obtained in Example 8, polyacrylamide gel electrophoresis (PAGE) was carried out on 9% (w/v) polyacrylamide slab gel (70 mm×80 mm, 1.0 mm thickness) making use of 150 mM tris-glycine buffer (pH: 8.8) as a running buffer in accordance with the method of Davis [B. J. Davis, *Ann. N. Y. Acad. Sci.*, 121, 404(1964)]. The electrophoresis was performed at 10 mA per gel for about 2 hours at room temperature. The proteins were then visualized by silver staining (kit of silver stain, product of Kanto Chemical Co., Inc.) in accordance with the method of Oakey et al. [B. R. Oakley, D. R. Kirsch and N. R. Morris, *Anal. Biochem.*, 105, 361(1980)].

Protein bands associated with carboxymethylcellulase activity were then visualized by active staining with Congo red. Namely, the slab gel after PAGE was placed on the surface of a CMC-agar plate and left over for 30 minutes at 37° C. in accordance with the method of Beguin [P. Beguin, *Anal. Biochem.*, 131, 333(1983)]. The CMC-agar plate was composed of 2% (w/v) of CMC (Sunrose A10MC), 3% (w/v) of NaCl, 10% (v/v) of 0.5M glycine-sodium hydroxide buffer (pH: 9.0) and 0.8% (w/v) of agar (product of Difco). This agar plate was stained with a 0.1% (w/v) Congo red (product of Wako Pure Chemical Industries, Ltd.)solution for 15 minutes at room temperature and then destained with a 1.0M NaCl solution for 15 minutes. As a result, a protein band having carboxymethylcellulase activity was detected at a position of 0.43 in terms of relative mobility (Rm).

Example 10

With respect to the crude enzyme solution obtained in Example 8, the isoelectric point (pI) was determined by PAGE in accordance with the method of Wringley [C. W. Wringley, *Methods Enzymol.*, 22, 559(1971)]. One hundred microliter of each enzyme solution (1 mg/ml) was electrophoresed in a 5% (w/v) acrylamide gel column containing 13.3 (w/v) of glycerol and 6.3% (v/v) of Pharmalyte (product of Pharmacia; pH range: 3–10) at a constant voltage of 200 V for about 15 hours. The cathode and anode were connected to an upper chamber (20 mM $H_3PO_4$) and a lower chamber (0.1M sodium hydroxide), respectively. After PAGE, the proteins were visualized by staining with 0.2% (w/v) Coomassie brilliant blue R-250 (product of Merck). Protein bands associated with carboxymethylcellulase activity were visualized by active staining in the same manner as in Example 9 to measure the relative mobility of an active band and to determine a pI value from a standard curve of known proteins. As a result, it was found to be pH 4.5.

Industrial Applicability

The enzymes according to this invention are broad in active pH range and active temperature range and are not inhibited by formulation ingredients for detergents, such as various surfactants, metal ions and proteinases. Therefore, they can be advantageously used as formulation components for detergent compositions.

We claim:

1. Carboxymethylcellulase 5430 having the following physicochemical properties:

(1) Action:

The carboxymethylcellulase 5430 can hydrolyze carboxymethylcellulose;

(2) Substrate specificity:

The carboxymethylcellulase 5430 shows strong activity toward carboxymethylcellulose and lichenan, and also is active toward cellulose powder, phosphoric acid-swollen cellulose, cellobiose, p-nitrophenol-$\beta$-D-glucopyranoside and p-nitrophenyl-$\beta$-D-cellobioside;

(3) Active pH range and optimum pH:

The carboxymethylcellulase 5430 is active in a pH range of 4.2–12.5 and has two optimum pH values of about 7.7 and about 9.5;

(4) pH Stability:

Even when kept overnight at 5° C., the carboxymethylcellulase 5430 is scarcely deactivated over a pH range of 4.6–12.8;

(5) Active temperature range and optimum temperature:

The carboxymethylcellulase 5430 is active over a temperature range of 10°–78° C., and its optimum temperature is at about 55° C.;

(6) Thermal stability:

The carboxymethylcellulase 5430 is scarcely deactivated even after being heated for 10 minutes at 60° C., and still retains some activity even after being heated to 80° C.;

(7) Effects of surfactants:

The activity of the carboxymethylcellulase 5430 is not inhibited by sodium dodecyl sulfate (SDS), sodium linear alkylbenzenesulfonate (LAS), sodium alkyl sulfate (AS), sodium polyoxyethylene alkyl sulfate (ES), sodium $\alpha$-olefin sulfonate (AOS), sodium $\alpha$-sulfonated fatty acid ester ($\alpha$-

SFE), fatty acid salt (soap) and polyoxyethylene alkyl ether;

(8) Molecular weight:

The molecular weight of the carboxymethylcellulase 5430 is 26,000±1,000 as estimated by gel filtration on Bio-Gel A 0.5 m, wherein said carboxymethylcellulase 5430 is isolated from Bacillus sp. PKM-5430 (FERM BP-4087).

* * * * *

UNITED STATES PATENT AND TRADEMARK OFFICE
CERTIFICATE OF CORRECTION

PATENT NO. : 5,439,816
DATED : August 8, 1995
INVENTOR(S) : Decorosa D. LUSTERIO, et al.

It is certified that error appears in the above-indentified patent and that said Letters Patent is hereby corrected as shown below:

On the title page, Item [87], the PCT Publishing Date should read:

--Jun. 24, 1993--

On the title page, Item [75], the first, second and fifth inventors' city of residence should read:

--Cagayan de Oro City--

Signed and Sealed this

Twenty-fourth Day of October, 1995

Attest:

BRUCE LEHMAN

*Attesting Officer*      *Commissioner of Patents and Trademarks*